(12) United States Patent
Hughes

(10) Patent No.: US 7,944,460 B2
(45) Date of Patent: May 17, 2011

(54) DEVICE AND METHOD FOR MARKING A CASSETTE FOR LABORATORY SAMPLES

(75) Inventor: Thomas Fergus Hughes, Eastbourne (GB)

(73) Assignee: Raymond A. Lamb Limited, Eastboune, East Sussex (GB)

( * ) Notice: Subject to any disclaimer, the term of this patent is extended or adjusted under 35 U.S.C. 154(b) by 250 days.

(21) Appl. No.: 12/300,834

(22) PCT Filed: May 18, 2007

(86) PCT No.: PCT/GB2007/001836
§ 371 (c)(1),
(2), (4) Date: Nov. 14, 2008

(87) PCT Pub. No.: WO2007/135388
PCT Pub. Date: Nov. 29, 2007

(65) Prior Publication Data
US 2009/0167835 A1  Jul. 2, 2009

(30) Foreign Application Priority Data
May 18, 2006 (GB) .................................. 0609899.0
Jun. 2, 2006 (GB) .................................. 0610941.7

(51) Int. Cl.
*B41J 2/22* (2006.01)
*B41J 2/23* (2006.01)

(52) U.S. Cl. .................................. 347/171; 400/124.01
(58) Field of Classification Search ............ 400/124.01, 400/124.16, 124.19, 124.24, 124.28, 124.29, 400/124.31; 347/171
See application file for complete search history.

(56) References Cited

U.S. PATENT DOCUMENTS

| 4,408,215 A | 10/1983 | Kitchen |
| 5,833,794 A | 11/1998 | Mayer |
| 2003/0049178 A1 | 3/2003 | Kiene et al. |

FOREIGN PATENT DOCUMENTS

| GB | 2 206 083 A | 12/1988 |
| GB | 2 235 163 A | 2/1991 |
| GB | 2 253 711 A | 9/1992 |

*Primary Examiner* — Huan H Tran
(74) *Attorney, Agent, or Firm* — Fay Sharpe LLP

(57) ABSTRACT

A device (1) suitable for marking a laboratory sample cassette (2) has a platen (6) with an aperture (7) and a cassette (2) is positioned so that a marking surface (3) of the cassette is aligned with the aperture (7). The device (1) also has a plurality of wires (9) with each wire (9) connected to a solenoid (11). An end (10) of each of the wires (9) is heated by a ceramic guide (12a) and selected ones of the heated wires (9) are oscillated once in a first direction (25) by their respective solenoids (11) to and from the aperture (7) to mark the marking surface (3). All the wires are then moved in a second direction transversely relative to the first direction (25) and selected wires are then oscillated once to mark the marking surface (3). This process is repeated until the required marking of the cassette marking surface (3) is completed.

23 Claims, 2 Drawing Sheets

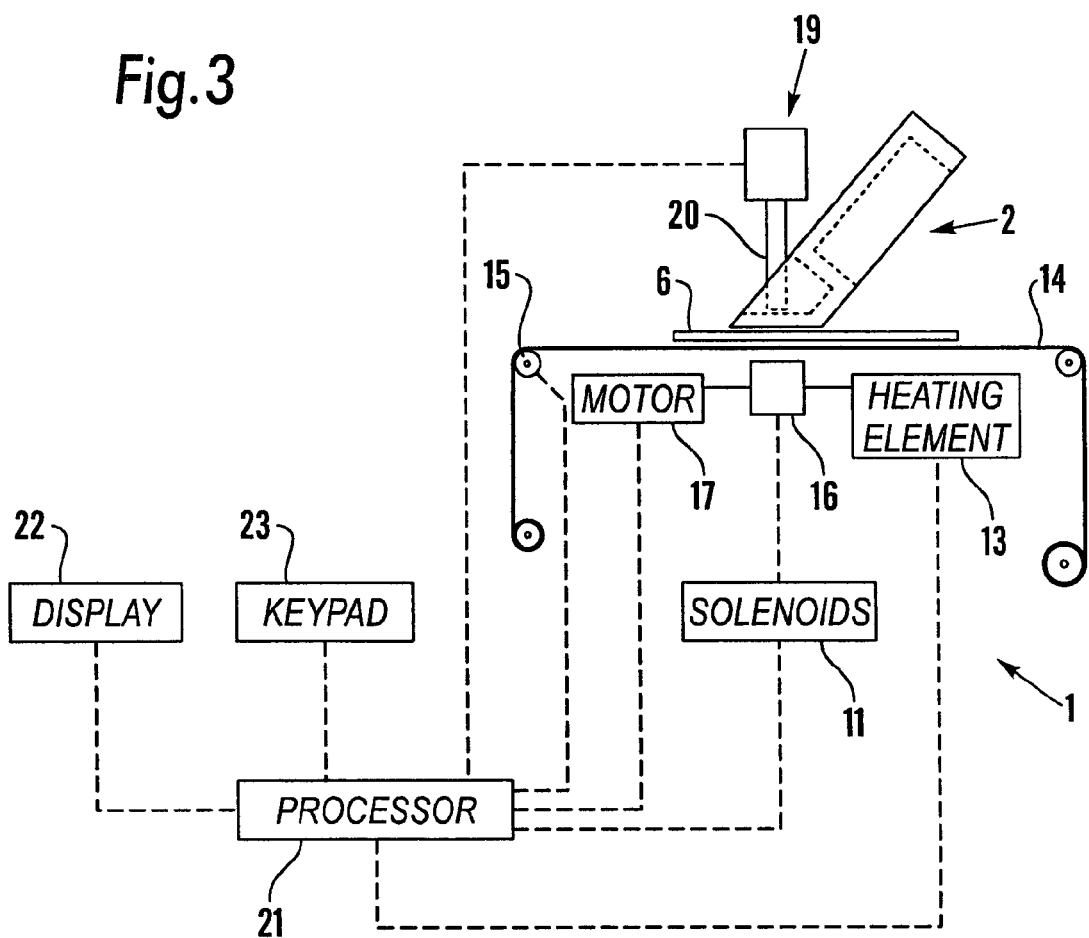

DEVICE AND METHOD FOR MARKING A CASSETTE FOR LABORATORY SAMPLES

CROSS-REFERENCE TO RELATED APPLICATIONS

This application is a national filing of International Application PCT/GB2007/001836, International Filing Date 18 May 2007, which claims the priority of GB0609899.0, filed on 18 May 2006 and GB0610941.7, filed on 2 Jun. 2006, which are hereby incorporated by reference in their entirety.

BACKGROUND OF THE INVENTION

The present invention relates to a device and method suitable for marking a laboratory sample cassette having a marking or writing surface.

A tissue processing laboratory sample cassette may have a marking surface disposed generally at an angle of 45° to the main body of the cassette. There are many cassettes on the market that have different physical properties. A clamp used to hold such a cassette so that its marking surface can be marked has to be adjusted to suit cassettes with different physical properties such as their shape.

GB-A-2235163 discloses a device for clamping and marking a laboratory sample cassette having a marking surface disposed at an angle to the main body of the cassette. An unmarked cassette is held by a clamp so that the writing surface is positioned to be marked by a stylus of a plotting mechanism. A foil tape is placed between the stylus and the cassette marking surface and the stylus is heated. Marking is produced on the marking surface by dragging the heated stylus over the foil tape.

A problem with the device is that the marking produced may not be that sharp. Also, there is a problem in that the foil tape can be damaged by dragging the stylus over it.

BRIEF SUMMARY OF THE INVENTION

It is an object of the present invention to provide a device and method to alleviate at least one of the above-mentioned problems.

According to one aspect of the present invention there is provided a device suitable for marking a laboratory sample cassette, comprising:

heating means for heating an end of at least one wire of the device;

oscillating means arranged to oscillate said at least one wire in a first direction to and from a marking location forming part of the device, the marking location arranged to receive a marking surface of the cassette; and translating means arranged to move the end of said at least one wire in a second direction transversely relative to the first direction.

The device enables the marking surface of a laboratory sample cassette to be marked by the pressure, temperature and oscillation of the at least one wire. This produces cleaner marking.

The device is arranged to mark plastic laboratory cassettes.

The device preferably includes a plurality of said wires with ends arranged substantially parallel and adjacent to each other and in a group, and the oscillating means is arranged to oscillate selected wires in the first direction. The wires may be arranged in a row substantially perpendicular to the first and second directions. The device preferably includes guide means for holding each said wire at a constant distance from adjacent wires.

The oscillating means may be arranged to oscillate the at least one wire at a frequency between 20,000 and 40,000 Hz. The high speed of oscillation aids cleaner marking. The amplitude of oscillatory movement of said at least one wire is preferably not more than 1 mm and may be substantially 0.25 mm.

The or each wire may have a particular diameter and the translating means is arranged to translate said at least one wire a distance substantially equal to said diameter during each oscillation cycle.

The oscillating means may comprise a solenoid for the or each wire.

The heating means may comprise a ceramic guide for said at least one wire. The ceramic guide is located close enough to the location so that the heat applied to the ceramic guide can be conducted to the end of the or each wire to enable it to mark the cassette marking surface. The ceramic guide may be located not more than 1 mm from the marking location and is preferably located within 0.2 mm of the marking location. The closer the heating means is to the end of the or each wire the better as the wire is of a small diameter which will cool very quickly.

The heating means is preferably arranged to heat said at least one wire to a temperature between 160° C. and 210° C.

The device may include means for positioning foil tape between the heating means and the marking location. By having the at least one wire oscillating so as to impact the positioned foil tape as opposed to being dragged along the tape, damage to the tape is minimised. The foil tape positioning means may include means for advancing the foil tape.

The device may include control means for controlling the process of marking the marking surface of a laboratory sample cassette received in the marking location.

The translating means of the device may be arranged to move said at least one wire substantially perpendicular to the first and second directions.

According to another aspect of the present invention there is provided a method suitable for marking a laboratory sample cassette comprising:

heating an end of at least one wire;

oscillating said at least one wire in a first direction to and from a location for receiving a marking surface of the cassette; and moving the end of said at least one wire in a second direction transversely relative to the first direction.

The method preferably includes receiving the marking surface of the laboratory sample cassette in said location.

The method may include providing a plurality of said wires with ends arranged substantially parallel and adjacent to each other and in a group, and the oscillating step includes oscillating selected wires in the first direction. The oscillating step may oscillate said at least one wire once in said first direction. The oscillating step is preferably followed by the wire end moving step and these two steps are repeated until marking of the cassette marking surface is completed.

The method may include the step of pre-heating the laboratory sample cassette. This improves the quality and speed of marking the cassette.

The method preferably uses a hot foil technique for marking the cassette.

BRIEF DESCRIPTION OF THE DRAWINGS

An embodiment of the present invention will now be described, by way of example, with reference to the accompanying schematic drawings, in which:

FIG. 3 is a view of the device showing a controlling processor.

DETAILED DESCRIPTION OF THE INVENTION

Figure 1:
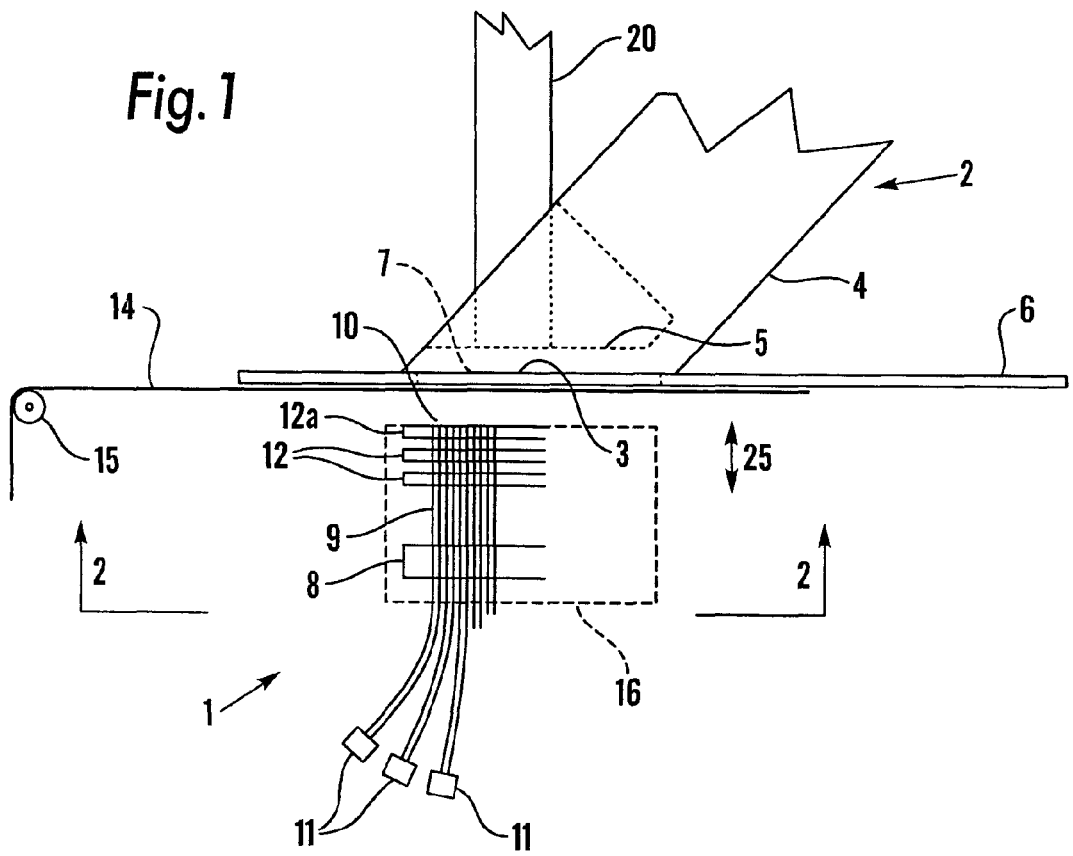
FIG. 1 is a side view of a cassette marking device according to one embodiment of the invention.
Figure 2:
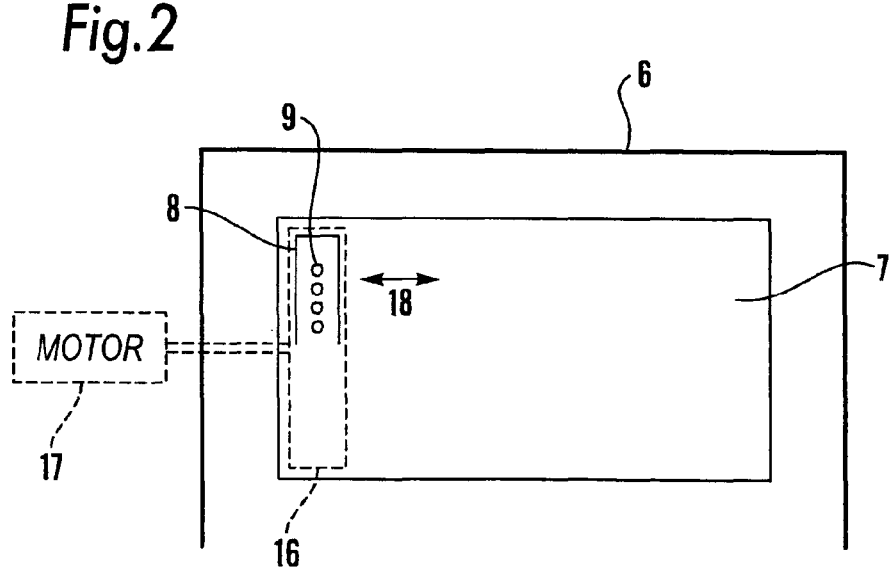
FIG. 2 is a view taken along line 2-2 of FIG. 1.

Referring to FIGS. 1 and 2 of the accompanying drawings, a device 1 is arranged to mark an injection moulded laboratory sample cassette 2 having a writing or marking surface 3 disposed at an inclined angle to the main body 4 of the cassette 2. The cassette 2 has a hollow space or recess 5 behind the marking surface 3 and is a laboratory tissue processing/embedding cassette.

The device 1 has a thin metal platen 6 with a cut-out or aperture 7 forming a marking region or location through which marking of the cassette marking surface 3 can occur.

A guide 8 holds a plurality of wires 9, the ends 10 of which are arranged in a row and each wire 9 is held at a fixed or constant distance or pitch from adjacent wires. Each wire 9 is connected to a solenoid 11 to oscillate the wire 9 in a first direction, shown by the arrow 25, to and from the marking surface 3.

Between the wire guide 8 and the platen 6 is a plurality of ceramic guides 12 through which the plurality of wires 9 pass and the ceramic guide 128 closest to the platen 6 is connected to a heating element 13 (see FIG. 3). The ceramic guide 12*a* is located close to the tips or ends 10 of the wires 9 facing the platen aperture 7 and a foil tape 14 is placed between the wire ends 10 and the aperture 7. The foil tape 14 can be moved by rollers 15.

The wire guide 8 and ceramic guides 12, 12*a* are held in a head 16 which is arranged to be moved by a motor 17 over the aperture 7 in a second direction shown by the arrow 18 in FIG. 2 (the foil tape having been omitted for clarity). The second direction 18 is perpendicular to the first direction of oscillation of the wires 9 and the row of wires 9 is perpendicular to both the first and second directions.

The device 1 is arranged to be used with a cassette clamp 19 which has a plunger 20 for being lowered into the recess 5 to urge the marking surface 3 towards the platen 6.

Referring to FIG. 3, the device 1 forms a stand-alone unit having an internal central processing unit (CPU) or control processor 21 connected to a display 22 and a control keypad 23. The control processor 21 is also connected to the solenoids 11, the head motor 17, the tape rollers 15 and the ceramic guide heating element 13 and the processor 21 can also control the cassette clamp 19.

In use, a laboratory sample cassette 2 is clamped by the clamp 19 so that the cassette marking surface 3 is aligned with the platen aperture 7 and is pinned against the platen 6 by the clamp plunger 20 engaging the recess 5 behind the marking surface 3.

The ceramic guide 12*a* is heated by the heating element 13 and the head 16 is placed in a start position over the aperture 7. An operator of the device 1 selects a particular reference to be marked on the cassette marking surface 3 by using the keypad 23 and the selected reference appears on the display 22.

To form the reference, selected ones of the wires 9 heated by the ceramic guide 12*a* are fired or longitudinally displaced by their respective solenoids 11 receiving appropriate signals from the control processor 21. The selected wires 9 oscillate once, impacting the foil tape 14 sandwiched between the wire ends 10 and the platen aperture 7. This causes the foil tape 14 to bond to the cassette marking surface 3 on the other side of the platen aperture 7 thus forming a mark. The head 16 is translated the distance equal to the diameter of one wire 9 along the direction of arrow 18 after the first selected wires 9 have been fired, selected wires 9 are fired to again impact the tape 14 and mark the cassette marking surface 3. This translation of the head 16 takes place during one oscillation cycle measured between successive impacts. This process is repeated until the required marking on the cassette marking surface 3 is completed.

When marking of the cassette 2 has finished, the cassette 2 is unclamped and removed. The head 16 is moved by the motor 17 back to the start position and the foil tape 14 is moved by the rollers 15 so that fresh tape 14 is advanced over the platen aperture 7.

In a specific example of a preferred embodiment, the wires 9 are heated to a temperature between 160° C. and 210° C. and the solenoids 11 cause the wires 9 to oscillate at a frequency between 20,000 and 40,000 Hz. The amplitude of oscillatory movement of each wire 9 is substantially 0.25 mm and the ceramic guide 12*a* in the head 16 is typically less than 0.2 mm from the platen 6 (in practise 0.02 mm).

Whilst a particular embodiment has been described, it will be understood that various modifications may be made without departing from the scope of the invention. For example, the head 16 may be moved perpendicularly to arrow 18 so that more than one line of marking can be made on a cassette marking surface 3. Instead of the device 1 having its own keypad and display, the device may be controlled by or have data sent to it by a personal computer (PC) or other device so as to operate like a conventional printer. Any suitable means may be used to enter the reference to be marked on a cassette 2.

The cassette 2 may be pre-heated before it is marked.

The invention claimed is:

1. A device (1) suitable for marking a laboratory sample cassette (2), comprising:
    a heater (12*a*, 13) arranged to heat an end (10) of at least one wire (9) of a plurality of wires with ends (10) arranged substantially parallel and adjacent to each other and in a group of the device (1);
    an oscillating mechanism (11) arranged to oscillate selected wires (9) in a first direction (25) to and from a marking location (7) forming part of the device (1), the marking location (7) arranged to receive a marking surface (3) of the cassette (2); and
    translating mechanism (16, 17) arranged to move the end (10) of said at least one wire (9) in a second direction (18) transversely relative to the first direction (25).

2. The device as claimed in claim 1, wherein the wires (9) are arranged in a row substantially perpendicular to the first and second directions (25, 18).

3. The device as claimed in claim 1, including a guide mechanism (12) arranged to hold each said wire (9) at a constant distance from adjacent wires.

4. The device as claimed in claim 1, wherein the oscillating mechanism (11) is arranged to oscillate the at least one wire (9) at a frequency between 20,000 and 40,000 Hz.

5. The device as claimed in claim 1, wherein the amplitude of oscillatory movement of said at least one wire (9) is not more than 1 mm.

6. The device as claimed in claim 5, wherein the amplitude of oscillatory movement of said at least one wire (9) is substantially 0.25 mm.

7. The device as claimed in claim 1, wherein the or each wire (9) has a particular diameter and wherein the translating mechanism (16, 17) is arranged to translate said at least one wire (9) a distance substantially equal to said diameter during each oscillation cycle.

8. The device as claimed in claim 1, wherein the oscillating mechanism comprises a solenoid (11) for the at least one wire (9).

9. The device as claimed in claim 1, wherein said heater comprises a ceramic guide (12a) for said at least one wire (9).

10. The device as claimed in claim 9, wherein the ceramic guide (12a) is located not more than 1 mm from the marking location (7).

11. The device as claimed in claim 10, wherein the ceramic guide (12a) is located within 0.2 mm of the marking location (7).

12. The device as claimed in claim 1, wherein the heater (12a, 13) is arranged to heat said at least one wire (9) to a temperature between 160° C. and 210° C.

13. The device as claimed in claim 1, including a positioning mechanism (15) arranged to position foil tape (14) between the heater (12a, 13) and the marking location (7).

14. The device as claimed in claim 13, wherein the foil tape positioning mechanism includes an advancing mechanism (15) arranged to advance the foil tape (14).

15. The device as claimed in claim 1, including a controller (21) arranged to control the process of marking the marking surface (3) of a laboratory sample cassette (2) received in the marking location (7).

16. The device as claimed in claim 1, wherein the translating mechanism (16, 17) is arranged to move said at least one wire (9) substantially perpendicular to the first and second directions (25, 18).

17. A method suitable for marking a laboratory sample cassette (2), comprising:

providing a plurality of wires (9) with ends (10) arranged substantially parallel and adjacent to each other and in a group;

heating an end (10) of at least one wire (9);

oscillating selected wires (9) in a first direction (25) to and from a location (7) for receiving a marking surface (3) of the cassette (2); and moving the end (10) of said at least one wire (9) in a second direction (18) transversely relative to the first direction (25).

18. The method as claimed in claim 17, wherein the oscillating step oscillates said at least one wire (9) once in said first direction.

19. The method as claimed in claim 17, including receiving the marking surface (3) of the laboratory sample cassette (2) in said location (7).

20. The method as claimed in claim 19, including pre-heating the cassette (2).

21. The method as claimed in claim 19, including using a hot foil technique to mark the cassette (2).

22. The method as claimed in claim 19, wherein the oscillating step is followed by the wire end moving step and these two steps are repeated until marking of the cassette marking surface (3) is completed.

23. A device (1) suitable for marking a laboratory sample cassette (2), comprising:

heating means (12a, 13) for heating an end (10) of at least one wire (9) of a plurality of wires with ends (10) arranged substantially parallel and adjacent to each other and in a group of the device (1);

oscillating means (11) arranged to oscillate selected wires (9) in a first direction (25) to and from a marking location (7) forming part of the device (1), the marking location (7) arranged to receive a marking surface (3) of the cassette (2); and translating means (16, 17) arranged to move the end (10) of said at least one wire (9) in a second direction (18) transversely relative to the first direction (25).

* * * * *